United States Patent [19]

Abdelrahman et al.

[11] Patent Number: 4,745,796
[45] Date of Patent: May 24, 1988

[54] MEMBRANE-SELECTIVE VAPOR SENSING

[75] Inventors: Mona Abdelrahman, Minnetonka; David W. Deetz, Apple Valley; J. David Zook, Burnsville, all of Minn.

[73] Assignee: Honeywell Inc., Minneapolis, Minn.

[21] Appl. No.: 26,096

[22] Filed: Mar. 16, 1987

[51] Int. Cl.$^4$ .............................................. G01N 27/00
[52] U.S. Cl. ........................................... 73/26; 55/158
[58] Field of Search ...................... 73/19, 23, 27 R, 26; 55/16, 158

[56] References Cited

U.S. PATENT DOCUMENTS

| | | | |
|---|---|---|---|
| 3,864,628 | 2/1975 | Klass et al. | 73/23 X |
| 4,040,805 | 8/1977 | Nelms et al. | 55/158 |
| 4,174,374 | 11/1979 | Matson | 55/16 X |
| 4,187,086 | 2/1980 | Walmet et al. | 55/16 |
| 4,268,279 | 5/1981 | Shidno et al. | 55/16 |
| 4,598,576 | 7/1986 | Goldsmith et al. | 73/19 |

OTHER PUBLICATIONS

Membrane Technology and Applications: An Assessment, Office of Scientific and Technical Information, United States Department of Energy, Stephen A. Leeper, et al., Feb. 1984.
Recent Developments in Separation Science, vol. 1, Norman N. Li, Sc. D., 1972.
Physical Chemistry of Surfaces, Fourth Edition, Arthur W. Adamson, 1982.

Primary Examiner—Stewart J. Levy
Assistant Examiner—Joseph W. Roskos
Attorney, Agent, or Firm—C. G. Mersereau

[57] ABSTRACT

Generic, non-selective sensors identify specific vapors of interest through selectively permeable ILMs which eliminate interfering species.

10 Claims, 3 Drawing Sheets

MEMBRANE-SELECTIVE VAPOR SENSING

BACKGROUND OF THE INVENTION

1. Field of the Invention

The present invention relates generally to a system for sensing the presence of certain chemical species in vapor form in a gaseous mixture and, more particularly, to the use of selectively permeable stabilized liquid membranes in combination with general purpose semiconductor or catalytic gas sensors to produce a selectively responsive analytic tool. That is, the detector sensing system of the invention is one in which the selectivity is enhanced by the permeability of the membrane or "permselectivity" rather than being based solely on particular selective adsorption or ion selectivity characteristics of the sensing element.

2. Description of the Prior Art

Relatively general purpose gas sensing elements and devices of various types have been in existence for some time. These include relatively non-selective or generic, stabilized solid state devices such as those exhibiting catalytic action to promote the oxidation of organic vapors at elevated temperatures. A semiconductor gas sensor, for example, composed mainly of tin dioxide ($SnO_2$) responds to reducing gases, including organic vapors, generally. A catalytic sensor such as a platinum wire or a platinum thin film configuration which might, for example, take the form of a microscopic bridge structure such as that structure shown in U.S. Pat. No. 4,624,137 is also in this category.

Such sensors are relatively inexpensive and perform admirably in many applications. However, sensitivity to common atmospheric variables has heretofore limited the scope of effective utility for these devices. $SnO_2$, for example, is highly sensitive to changes in the level of relative humidity in the sensing environment. In addition, all such sensors are sensitive to flow and changes in the velocity of the sensed vapors. These and other phenomena produce changes in sensor output, thereby introducing error in the readings.

Of course, generic sensors inherently lack selectivity. This lack of selectivity may not be a primary drawback in certain applications where, for instance, a single species is being monitored in a known mixture. However, many gases can produce sensor responses of like or even order and, therefore, interference possibilities have always required attention.

Thus, definite needs exist in the art for sensing systems which can take advantage of the sensitivity and relatively low cost of relatively non-selective generic sensors such as tin oxide notwithstanding common interfering species in the sample atmosphere.

SUMMARY OF THE INVENTION

The present invention solves long-standing prior art problems surrounding the application of generic type, stabilized solid state sensors to sense the presence of species of interest in situations where interfering species, such as water vapors and interfering conditions, such as sample flow past the sensor, heretofore have rendered discreet measurements difficult or not possible. The present invention is, in its broader sense, directed to the combination of a generic, i.e., relatively non-selective or non-specific sensor with a stabilized, immobilized liquid membrane of desired selective permeability. The membrane is interposed between the ambient environment of the species of interest sought to be measured and the environment of the sensing element itself and acts as a selective filter with respect to the species of interest. The sensing element is, typically, located in a chamber or cell having a single access sealed by the membrane. The element then, is maintained in a selective stable isolation with respect to the external environment in which the membrane allows the species of interest to pass unaffected into the sensor chamber to the exclusion of interfering species. Of course, the sensor is also removed from the presence of any flowing sample stream which might produce measurement aberrations.

While other combinations are contemplated, the invention is illustrated by preferred embodiments in which a tin oxide ($SnO_2$) gas sensor element is combined with an immobilized liquid membrane (ILM) of a porous polymer, the pores of which contain a hydrophobic organic liquid having a high permeability for certain gases or vapors, namely, organic vapors, and the ability to repel the interfering species such as water vapor. This allows the sensor element to sense the presence of organics such as those present in tobacco smoke in ambient air readily and without interference.

The selective membrane preferred for the illustrative embodiment is one made substantially of polypropylene having a frame or membrane thickness of about 25 microns and a nominal pore size of 0.02 microns in a micro-tear configuration. One such material is sold under the trademark Celgard by Celanese Corporation, New York, NY.

An alternative selective membrane is in the form of composite membrane in which an ultra-thin (0.1–1.5 micron) microporous (pore size one micron or less) "skin" outer layer is supported on a relatively thick (approximately 100 microns) macroporous polymer matrix. The ultra-thin or skin matrix contains a selective transport liquid.

In either case, the pores of the microporous membrane matrix are filled with a hydrophobic, low vapor pressure, chemically compatible liquid which wets the matrix material and has a high solubility and diffusivity for the organic species of interest. The preferred liquid is a dimethyl-silicone oil which is virtually 100 percent miscible with most of the organic contaminates of interest in tobacco smoke and has negligible vapor pressure at room temperature which leads to long term stability.

The membrane and sensor of the invention are preferably combined in a system including a sensing cell having a sample inlet covered by the selective membrane and containing the sensor element. The sensor output based on the quanitative presence of species of interest may be in terms of a voltage or other converted electrical signal using conventional techniques and circuitry well known to those skilled in the art. Any conventional output means can be used.

DESCRIPTION OF THE PREFERRED EMBODIMENT

Figure 1:
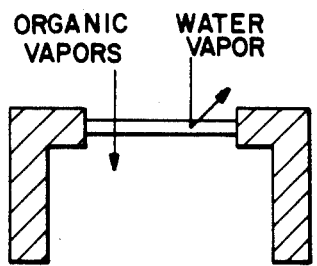
FIG. 1 is a cross-sectional view illustrating a hydrophobic selective membrane.

FIG. 1 depicts schematically the preferential transport of organic vapors to the exclusion of water vapor with respect to the membrane of the preferred embodiment. As noted above, the selectivity is determined by the permeability of the membrane (permselectivity) rather than selective absorption or ion selectivity. This utilizes principles with respect to miscibility and transport of vapor molecules across liquid membranes which can be used to achieve very rapid and very selective transport. Selective transport of species across such liquid membranes, generally, is discussed in greater detail in co-pending application Ser. No. 025,920, now U.S. Pat. No. 4,710,205, filed of even date, also by David C. Deetz, herein a co-inventor, and is assigned to the same assignee denoting common ownership with the present invention. To the extent required, details in that application are hereby incorporated by reference in the present application.

As previously explained, the liquid filling the pores in the microporous membrane is one selected to facilitate the transport of the species of interest to the exclusion of interfering species. In addition, the liquid must also be chemically compatible with the other components of the cell and external environments. The liquid also must have a low enough vapor pressure at the operating temperature of the system to achieve long-term stability of the liquid membrane. This may be achieved by inherent low vapor pressure or through Kelvin effect lowering of the vapor pressure.

The preferred combination for the detection of organic vapors eminating from tobacco smoke includes dimethyl-silicone oil in a microporous matrix of polypropylene. The dimethyl-silicone oil is hydrophobic and has excellent transport properties with respect to the aldehydes, ketones and other irritant constituents of tobacco smoke. It also has an extremely low vapor pressure at ordinary room temperature.

Examples of other combinations which may be utilized, however, for other applications, include both aqueous and non-aqueous liquid based systems. The only limitations are the previously recited physical and chemical properties required of the system together with the desired transport and exclusion properties. The preferred embodiment with regard to tobacco smoke or organic vapor sensing, for example, utilizes a single membrane layer containing a viscous low vapor pressure liquid transport medium. That embodiment is preferred but certainly not exclusive. Other applications may utilize a two-layered system in which an ultra-thin (1 micron or less) membrane layer is supported on a macroporous polymer matrix underlayer which may be several orders of magnitude thicker than the ultra-thin layer.

Figure 2:
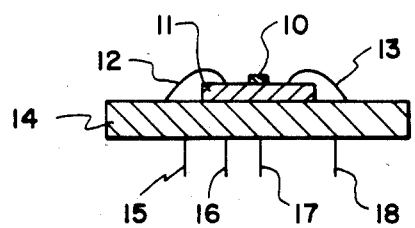
FIG. 2 shows a detector element with a mounting base.

FIG. 2 illustrates a typical sensor of the type which may be utilized in the sensing system of the invention. This includes a very small sensing element 10 which may be mounted on an insulating material 11 and is connected by sensing leads (normally of noble metal) 12 and 13. A heater, not shown, is utilized to externally heat the element to a temperature (nominally 450° C. in the case of tin oxide) in the range of highest operating sensitivity. The element can be further mounted in a resin molding such as shown at 14 through which heating and sensing connections 15, 16, 17 and 18 protrude. One typical sensor which has been used successfully is a TGS 812 sold by Figaro, USA, Inc. of Wilmette, Ill.

Figure 3:
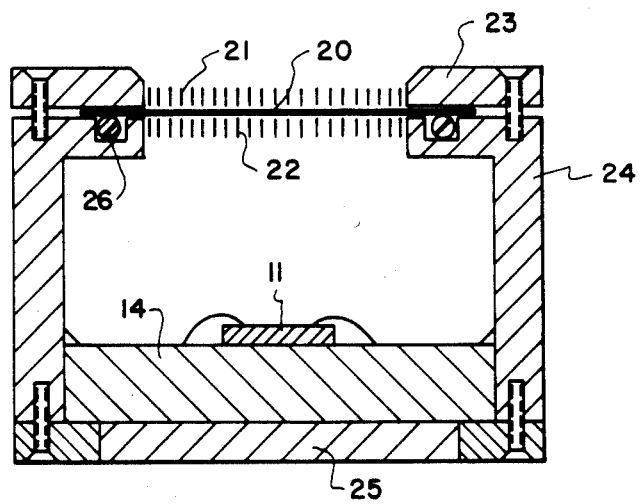
FIG. 3 is a cross-sectional view through a typical sensing cell in accordance with the present invention.

FIG. 3 depicts cross-sectional view of a typical sensing system utilizing the invention. It includes the microporous membrane 20 sandwiched between a pair of supports which may be layers of plastic mesh as illustrated at 21 and 22. They protect the membrane from damage and give it the necessary strength to span the top opening of the cell. The membrane and mesh is retained between an upper retaining plate 23 and a body member 24 which may be anodized aluminum, or other sufficiently rigid, compatible material. A base plate member is provided at 25 to retain the resin molding 14 of the element subsystem and the cell is assembled as by utilizing the illustrated screws together with a sealing O-ring as illustrated by 26.

Figure 4:
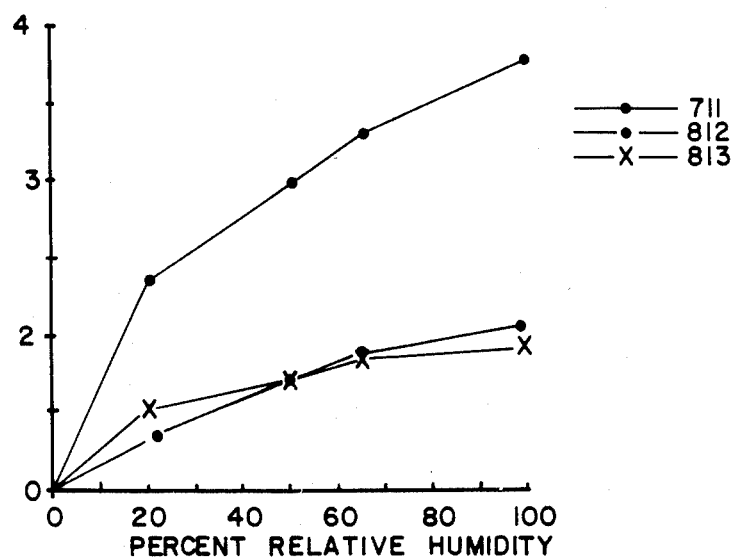
FIG. 4 graphically illustrates the effect of changes in relative humidity on the response of several tin oxide sensors.

FIG. 4 depicts a graph of the reaction of three different models of Figaro tin oxide sensors to changes in relative humidity. It shows a wide variance in reaction to humidity between different models of sensors, but it also illustrates the fact that all the tin oxide sensors are quite sensitive to changes in relative humidity.

Figure 5:
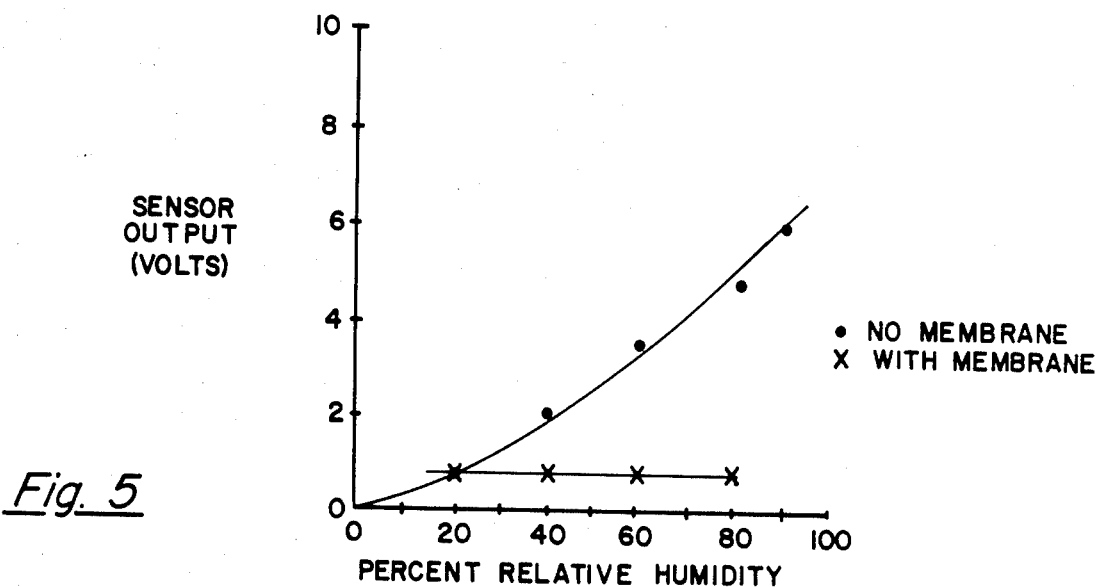
FIG. 5 compares sensor output with percent relative humidity for an unprotected sensor and one protected by a membrane fixing the relative humidity at about 20 percent.

FIG. 5 depicts graphically the effect of tin oxide sensor voltage output in relation to changes in percent relative humidity with and without the use of the selective membrane in accordance with the present invention. It can readily be seen that once the system is provided with the membrane, the relative humidity within the chamber will remain constant despite wide variances in the humidity of the external environment. It should also be noted that the relative humidity of the environment at the time the unit is sealed, e.g., 20%, may determine the baseline output voltage of the system itself, which at 20 percent relative humidity is slightly under one volt. Of course, such devices can be assembled in an environment of controlled humidity, if desired.

Figure 6:
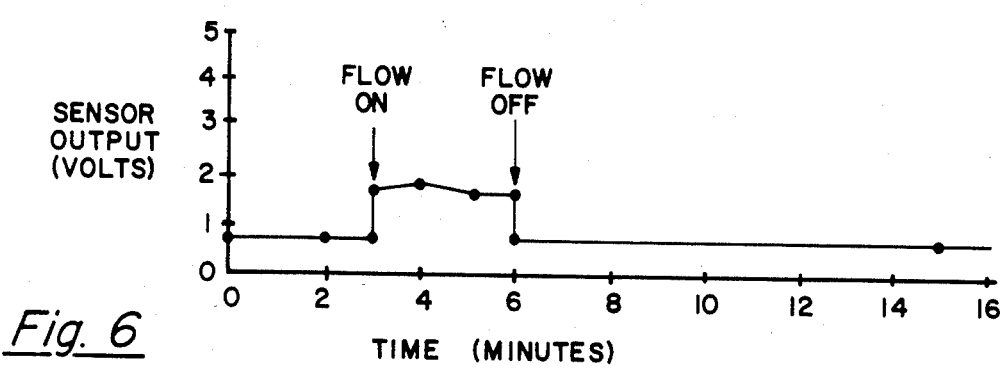
FIGS. 6 and 7 illustrate the effect of flow on the sensor base line output.
Figure 7:
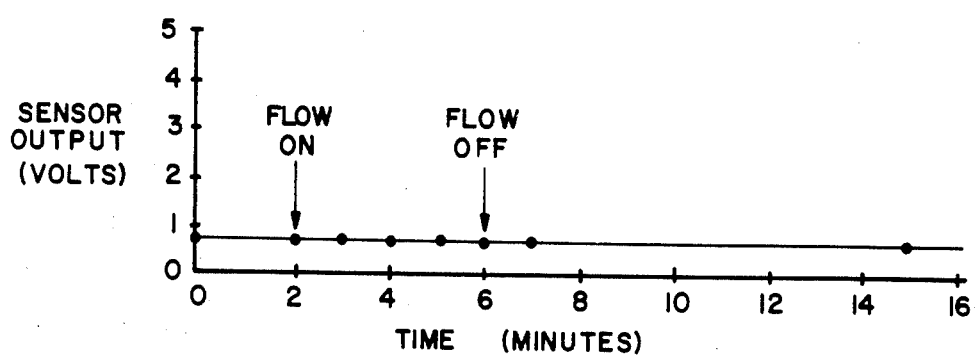

FIGS. 6 and 7 are included to show the reaction of a typical tin oxide generic sensor to flow. In the open system of FIG. 6, a definite step change increasing the output of the sensor is noted upon impingement of flow and likewise a step change down is noted upon removal of the flow. FIG. 7 shows the stabilizing effect of the membrane which, of course, prevents flow impingement on the sensor.

Figure 8:
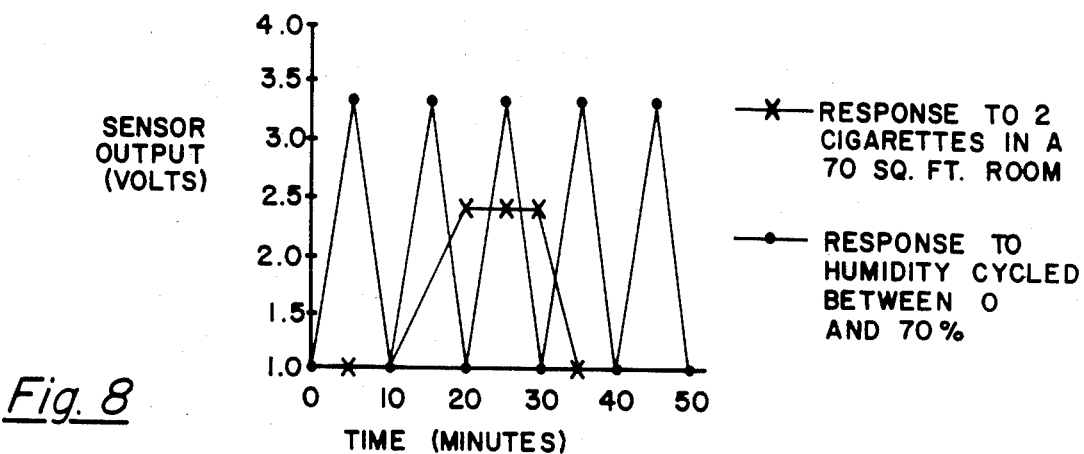
FIGS. 8 and 9 show sensor response to combined tobacco smoke and cycled relative humidity without and with selective membranes.
Figure 9:
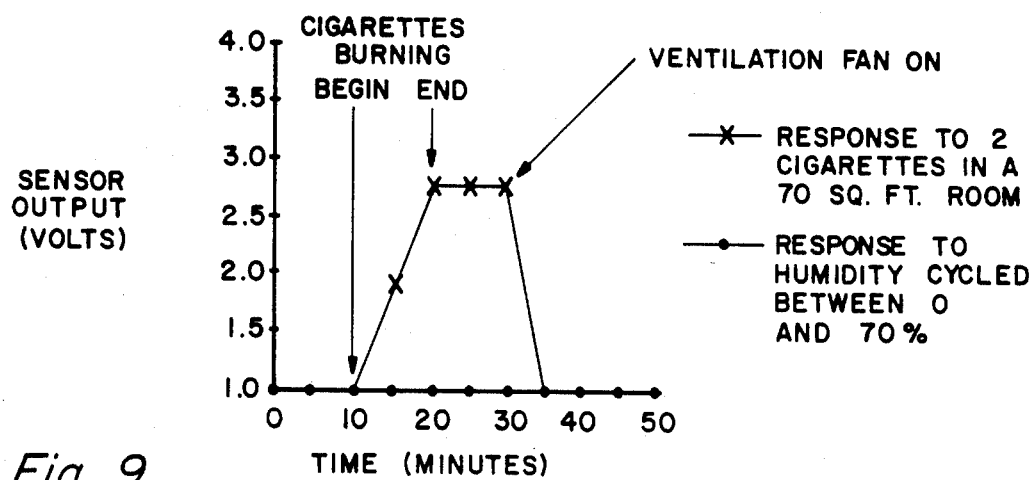

FIGS. 8 and 9 address the extreme high sensitivity of the sensing system of the invention to organic constituents contained in tobacco smoke. Note, however, that the response is almost entirely wiped out or overshadowed by the cycled relative humidity superimposed in FIG. 8 for a system without the membrane and is very pronounced with respect to the system containing the membrane illustrated in FIG. 9.

As explained above, the membrane sensor combination of the preferred embodiment utilizing the dimethyl-silicone oil liquid is particularly successful in conveying organic molecules and repelling water molecules. The detection system is extremely sensitive to smoke components which include compounds and derivatives including pyridine, acrolein, and furfural. The system is also extremely sensitive to acetone. It should be remembered, however, that the detector itself is non-specific and depends on the dynamics of the ILM to exclude interfering species while transporting species of interest.

Without further elaboration, it is believed that one skilled in the art can, using the preceding description together with the enumerated preferred specific embodiments, utilize the present invention to its fullest extent. Therefore, the preferred specific embodiments are to be construed as merely illustrative and not limitative of the remainder of the disclosure in any way whatsoever.

What is claimed is:

1. A system for detecting at least one species of interest in vapor form comprising:
    enclosure means describing a hollow chamber and having an opening therein providing direct communication between the chamber and the external environment;
    sensor means disposed within the chamber and having an output signal responsive to the presence of one or more of said species of interest;
    stabilized immobilized liquid membrane matrix disposed across and covering said opening having pores therein forming a porous structure disposed across and covering said opening, said liquid membrane further comprising a permselective transport liquid in and wetting said pores, said liquid characterized by permselective transport properties which favor said one or more species of interest;
    output means for generating a signal indicative of the species of interest based on the output signal of said non-selective sensor; and
    conductor means connecting said sensor means with said output means.

2. The system of claim 1 wherein said membrane is microporous polypropylene.

3. The system of claim 2 wherein said transport liquid is an organic liquid.

4. A system for detecting organic vapor species of interest in ambient air comprising:
    enclosure means describing a hollow chamber and having an opening therein providing direct communication between the chamber and the external environment;
    a non-selective sensor means, consisting substantially of a chemically sensitive resistor having an electrical signal sensitive to the presence of the organic vapor species of interest, disposed within the chamber;
    a permselective, stabilized immobilized liquid membrane matrix, having a porous structure, disposed across and covering said opening, wherein said liquid membrane further comprises a non-volatile, non-aqueous, hydrophobic transport liquid in said pores, said liquid characterized by permselective transport properties favoring the migration of said one or more species of interest and the ability to wet the material of said pores;
    output means for generating a signal indicative of the species of interest based on the output signal of said non-selective sensor; and
    conductor means connecting said sensor means with said output means.

5. The system of claim 4 wherein said membrane is microporous polypylene.

6. The system of claim 4 wherein said transport liquid is an organic liquid.

7. A system for detecting the presence of tobacco smoke in ambient air comprising:
    enclosure means describing a hollow chamber having an opening therein for comunicating with the environment without the chamber;
    sensor means consisting substantially of tin oxide (SnO$_2$) disposed within the chamber;
    a permselective, stabilized immobilized liquid membrane matrix, having a porous structure, disposed across and covering said opening, said liquid membrane further comprising a non-volatile low vapor pressure, hydrophobic organic transport liquid in said pores, said liquid characterized by permselective transport properties favorable to the one or more organic species of interest and the ability to wet the material of said matrix;
    output means for generating an output signal based on the sensor output quantitatively indicative of the presence of the one or more organic species of interest;
    conductor means connecting said sensor means with said output means.

8. The system of claim 7 wherein said membrane is microporous polypropylene.

9. The system of claim 7 wherein said transport liquid is an organic liquid.

10. The system of claim 9 wherein said transport liquid is dimethyl silicone oil.

* * * * *